United States Patent
Erbulut et al.

(10) Patent No.: US 10,188,431 B2
(45) Date of Patent: Jan. 29, 2019

(54) DOUBLE-HEADED PEDICLE SCREW

(71) Applicants: Deniz Ufuk Erbulut, Istanbul (TR); Suleyman Keles, Izmir (TR); Ali Fahir Ozer, Istanbul (TR)

(72) Inventors: Deniz Ufuk Erbulut, Istanbul (TR); Suleyman Keles, Izmir (TR); Ali Fahir Ozer, Istanbul (TR)

( * ) Notice: Subject to any disclaimer, the term of this patent is extended or adjusted under 35 U.S.C. 154(b) by 95 days.

(21) Appl. No.: 15/383,021

(22) Filed: Dec. 19, 2016

(65) Prior Publication Data
US 2017/0172628 A1 Jun. 22, 2017

Related U.S. Application Data

(60) Provisional application No. 62/268,701, filed on Dec. 17, 2015.

(51) Int. Cl.
*A61B 17/70* (2006.01)

(52) U.S. Cl.
CPC ........ *A61B 17/7034* (2013.01); *A61B 17/704* (2013.01); *A61B 17/7032* (2013.01); *A61B 17/7038* (2013.01)

(58) Field of Classification Search
CPC ............ A61B 17/7034; A61B 17/7032; A61B 17/7035; A61B 17/7038; A61B 17/7043; A61B 17/7049; A61B 17/705
See application file for complete search history.

(56) References Cited

U.S. PATENT DOCUMENTS

| | | | |
|---|---|---|---|
| 4,946,458 A | 8/1990 | Harms et al. |
| 5,196,013 A | 3/1993 | Harms et al. |
| 5,207,678 A | 5/1993 | Harms et al. |
| 5,443,467 A | 8/1995 | Biedermann et al. |
| 5,466,237 A | 11/1995 | Byrd, III et al. |
| 5,474,551 A | 12/1995 | Finn et al. |
| 5,474,555 A | 12/1995 | Puno et al. |
| 5,520,690 A | 5/1996 | Errico et al. |
| 5,531,746 A | 7/1996 | Errico et al. |
| 5,591,166 A | 1/1997 | Bernhardt et al. |
| 5,607,426 A | 3/1997 | Ralph et al. |
| 5,628,740 A | 5/1997 | Mullane |
| 5,669,911 A | 9/1997 | Errico et al. |
| 5,672,176 A | 9/1997 | Biedermann et al. |
| 5,683,392 A | 11/1997 | Richelsoph et al. |
| 5,690,630 A | 11/1997 | Errico et al. |
| 5,728,098 A | 3/1998 | Sherman et al. |
| 5,797,911 A | 8/1998 | Sherman et al. |
| 5,800,435 A | 9/1998 | Errico et al. |
| 5,810,819 A | 9/1998 | Errico et al. |

(Continued)

FOREIGN PATENT DOCUMENTS

WO 2010/036949 A2 4/2010

*Primary Examiner* — Julianna N Harvey
(74) *Attorney, Agent, or Firm* — MacMillan, Sobanski & Todd, LLC (57) ABSTRACT

A double-headed pedicle screw is provided. The double-headed pedicle screw includes a threaded shaft portion and a plurality of yoke assemblies supported by the threaded shaft portion. Each of the yoke assemblies includes a recess configured to receive a portion of a rod, alignment structure, or immobilization structure therein. Each of the yoke assemblies is configured for pivoting movement relative to the threaded shaft portion independent of the pivoting movement of the other yoke assemblies.

11 Claims, 7 Drawing Sheets

(56) References Cited

U.S. PATENT DOCUMENTS

| | | |
|---|---|---|
| 5,863,293 A | 1/1999 | Richelsoph |
| 5,879,350 A | 3/1999 | Sherman et al. |
| 5,891,145 A | 4/1999 | Morrison et al. |
| 5,961,517 A | 10/1999 | Biedermann et al. |
| 5,964,760 A | 10/1999 | Richelsoph |
| 6,053,917 A | 4/2000 | Sherman et al. |
| 6,090,111 A | 7/2000 | Nichols |
| 6,113,601 A | 9/2000 | Tatar |
| 6,132,432 A | 10/2000 | Richelsoph |
| 6,146,383 A | 11/2000 | Studer et al. |
| 6,280,442 B1 | 8/2001 | Barker et al. |
| 6,368,321 B1 | 4/2002 | Jackson |
| 6,471,705 B1 | 10/2002 | Biedermann et al. |
| 6,482,207 B1 | 11/2002 | Errico |
| 6,485,494 B1 | 11/2002 | Haider |
| 6,488,681 B2 | 12/2002 | Martin et al. |
| 6,540,748 B2 | 4/2003 | Lombardo |
| 6,565,565 B1 | 5/2003 | Yuan et al. |
| 6,565,567 B1 | 5/2003 | Haider |
| 6,585,740 B2 | 7/2003 | Schlapfer et al. |
| 6,660,004 B2 | 12/2003 | Barker et al. |
| 6,733,502 B2 | 5/2004 | Altarac et al. |
| 6,858,030 B2 | 2/2005 | Martin et al. |
| 7,141,051 B2 | 11/2006 | Janowski et al. |
| 7,875,065 B2 | 1/2011 | Jackson |
| 8,137,387 B2 | 3/2012 | Garamszegi |
| 8,197,518 B2 | 6/2012 | Hammill, Sr. et al. |
| 8,241,341 B2 | 8/2012 | Walker et al. |
| 8,398,682 B2 | 3/2013 | Jackson et al. |
| 8,657,858 B2 | 2/2014 | Garamszegi et al. |
| 8,790,374 B2 | 7/2014 | Iott et al. |
| 8,852,239 B2 | 10/2014 | Jackson et al. |
| 8,882,809 B2 | 11/2014 | Walker et al. |
| 8,894,691 B2 | 11/2014 | Iott et al. |
| 8,940,024 B2 | 1/2015 | Biedermann et al. |
| 8,998,959 B2 | 4/2015 | Jackson et al. |
| 9,155,568 B2 | 10/2015 | Biedermann et al. |
| 9,179,937 B2 | 11/2015 | Iott et al. |
| 9,198,694 B2 | 12/2015 | Mishra et al. |
| 9,254,151 B2 | 2/2016 | Walker et al. |
| 9,259,254 B2 | 2/2016 | Iott et al. |
| 9,345,519 B1 | 5/2016 | Poirier et al. |
| 2002/0138077 A1* | 9/2002 | Ferree ............... A61B 17/7005 606/258 |
| 2004/0111088 A1 | 6/2004 | Picetti et al. |
| 2007/0250061 A1* | 10/2007 | Chin ............... A61B 17/7001 606/86 A |
| 2008/0306552 A1 | 12/2008 | Winslow et al. |
| 2009/0076552 A1 | 3/2009 | Tornier |
| 2009/0182384 A1 | 7/2009 | Wilcox et al. |
| 2011/0245883 A1* | 10/2011 | Dall ............... A61B 17/7035 606/305 |
| 2011/0257690 A1 | 10/2011 | Rezach |
| 2011/0270314 A1 | 11/2011 | Mueller et al. |
| 2012/0016425 A1 | 1/2012 | Shaffrey et al. |
| 2012/0221053 A1 | 8/2012 | Copf |
| 2012/0303072 A1 | 11/2012 | Eisermann |

* cited by examiner

DOUBLE-HEADED PEDICLE SCREW

CROSS-REFERENCE TO RELATED APPLICATION

This application claims the benefit of U.S. Provisional Application No. 62/268,701, filed Dec. 17, 2015, the disclosure of which is incorporated herein in its entirety by reference.

BACKGROUND

This invention relates in general to spinal fixation devices. A variety of spinal fixation devices are known for treating scoliosis, spondylolisthesis, degenerative disc disease, vertebra fractures, and other spinal disorders or abnormalities. In many instances, such spinal fixation devices include one or more pedicle screws. A typical pedicle screw includes a threaded shaft portion having a yoke-shaped head portion extending therefrom. The threaded shaft portion is adapted to be secured to a vertebra of the spine, while the head portion is adapted to be connected to a rod or other alignment or immobilization structure.

When used for treatment of spinal disorders or abnormalities, one or more pedicle screws are individually secured to the vertebrae of the spine to provide anchor points that can then be connected together with the rod or other alignment or immobilization structure. However, known pedicle screws do not allow movement of the pedicle screw during flexion and extension of the spine. This may create discomfort for a patient being treated using the pedicle screws.

Therefore, it would be desirable to provide a pedicle screw that allows movement of the pedicle screw during flexion and extension of the spine.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the double-headed pedicle screw.

The above objects as well as other objects not specifically enumerated are achieved by a double-headed pedicle screw. The double-headed pedicle screw includes a threaded shaft portion and a plurality of yoke assemblies supported by the threaded shaft portion. Each of the yoke assemblies includes a recess configured to receive a portion of a rod, alignment structure, or immobilization structure therein. Each of the yoke assemblies is configured for pivoting movement relative to the threaded shaft portion independent of the pivoting movement of the other yoke assemblies.

Various aspects of the double-headed pedicle screw will become apparent to those skilled in the art from the following detailed description, when read in light of the accompanying drawings.

DETAILED DESCRIPTION

The double-headed pedicle screw will now be described with occasional reference to specific embodiments. The double-headed pedicle screw may, however, be embodied in different forms and should not be construed as limited to the embodiments set forth herein. Rather, these embodiments are provided so that this disclosure will be thorough and complete, and will fully convey the scope of the double-headed pedicle screw to those skilled in the art.

Unless otherwise defined, all technical and scientific terms used herein have the same meaning as commonly understood by one of ordinary skill in the art to which the double-headed pedicle screw belongs. The terminology used in the description of the double-headed pedicle screw herein is for describing particular embodiments only and is not intended to be limiting of the double-headed pedicle screw. As used in the description of the double-headed pedicle screw and the appended claims, the singular forms "a," "an," and "the" are intended to include the plural forms as well, unless the context clearly indicates otherwise.

Unless otherwise indicated, all numbers expressing quantities of dimensions such as length, width, height, and so forth as used in the specification and claims are to be understood as being modified in all instances by the term "about." Accordingly, unless otherwise indicated, the numerical properties set forth in the specification and claims are approximations that may vary depending on the desired properties sought to be obtained in embodiments of the double-headed pedicle screw. Notwithstanding that the numerical ranges and parameters setting forth the broad scope of the double-headed pedicle screw are approximations, the numerical values set forth in the specific examples are reported as precisely as possible. Any numerical values, however, inherently contain certain errors necessarily resulting from error found in their respective measurements.

In accordance with the illustrated embodiments, the description and figures disclose a double-headed pedicle screw (hereafter "pedicle screw"). In certain embodiments, the pedicle screw includes a threaded shaft portion and a plurality of yoke assemblies. Each of the yoke assemblies are supported on the shaft portion for independent pivoting movement relative to the shaft portion. Each of the yoke assemblies has a recess adapted to receive a portion of a rod, alignment structure, or immobilization structure therein.

The terms "double-headed pedicle screw" or "pedicle screw", as used herein, is defined to mean any fastener attached to a vertebra of the spine, and connected to a rod or other alignment or immobilization structure.

Figure 1:
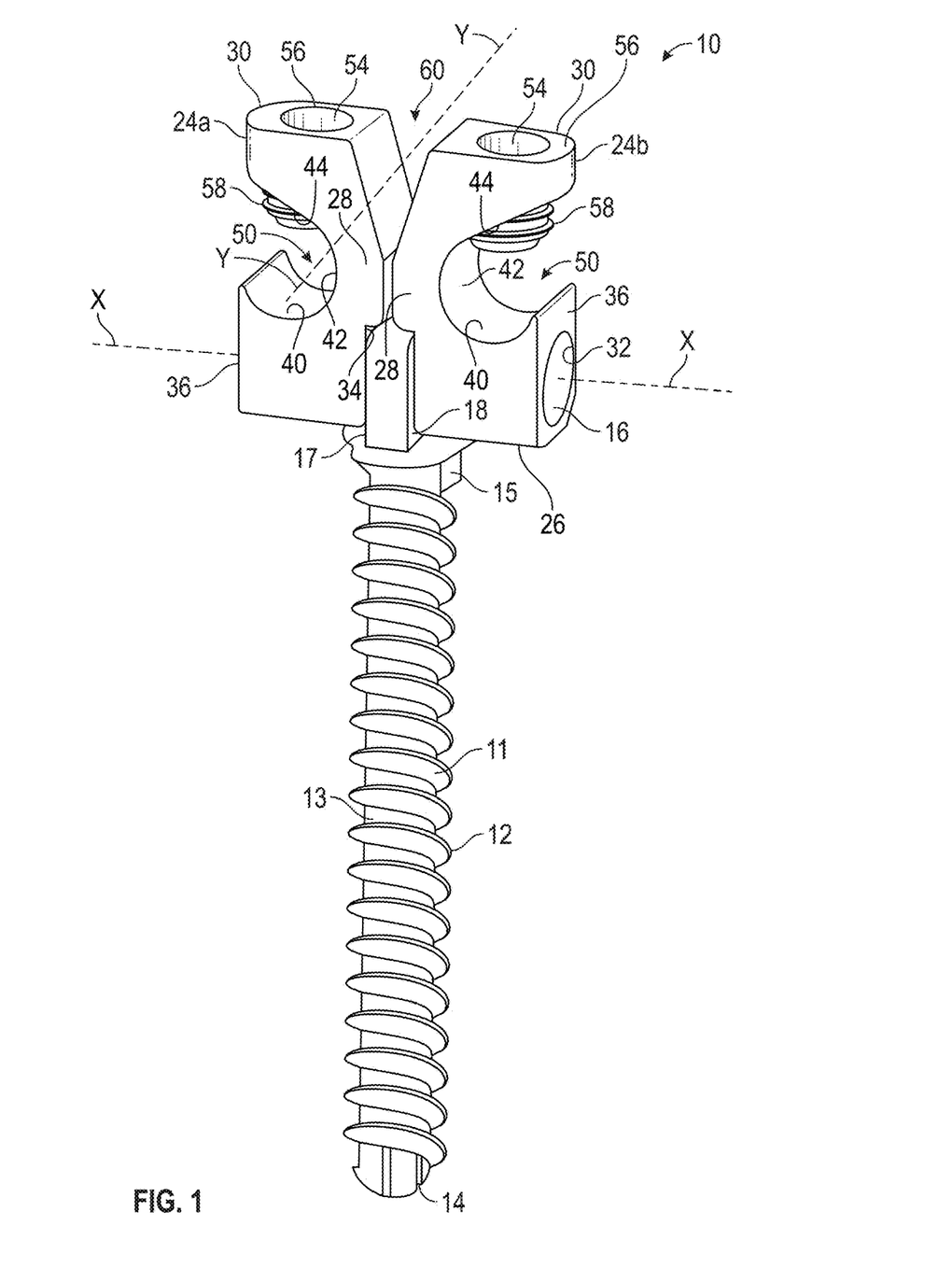
FIG. 1 is a perspective view of a first embodiment of a double-headed pedicle screw.
Figure 2:
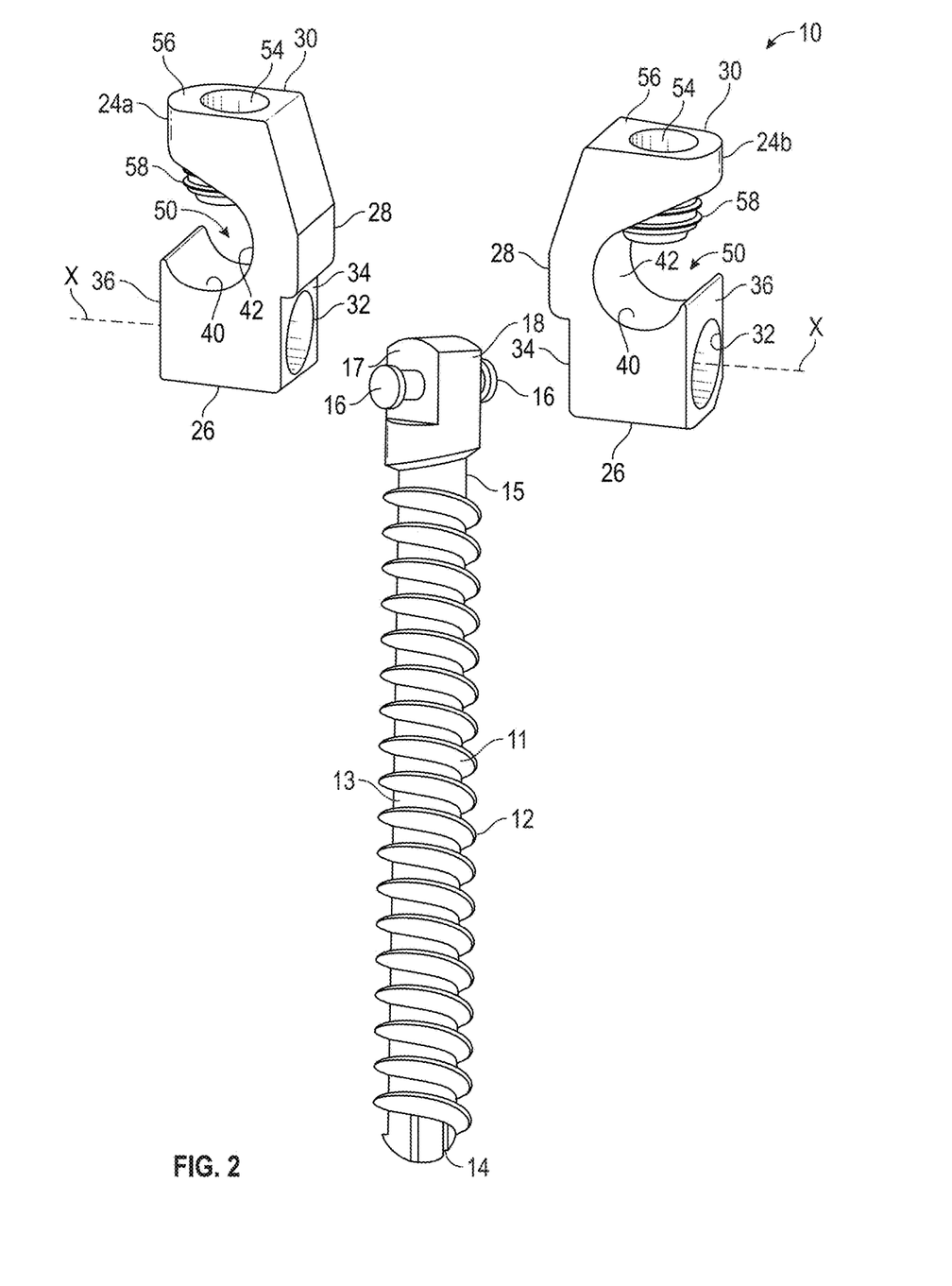
FIG. 2 is an enlarged, exploded perspective view of the double-headed pedicle screw illustrated in FIG. 1.
Figure 3:
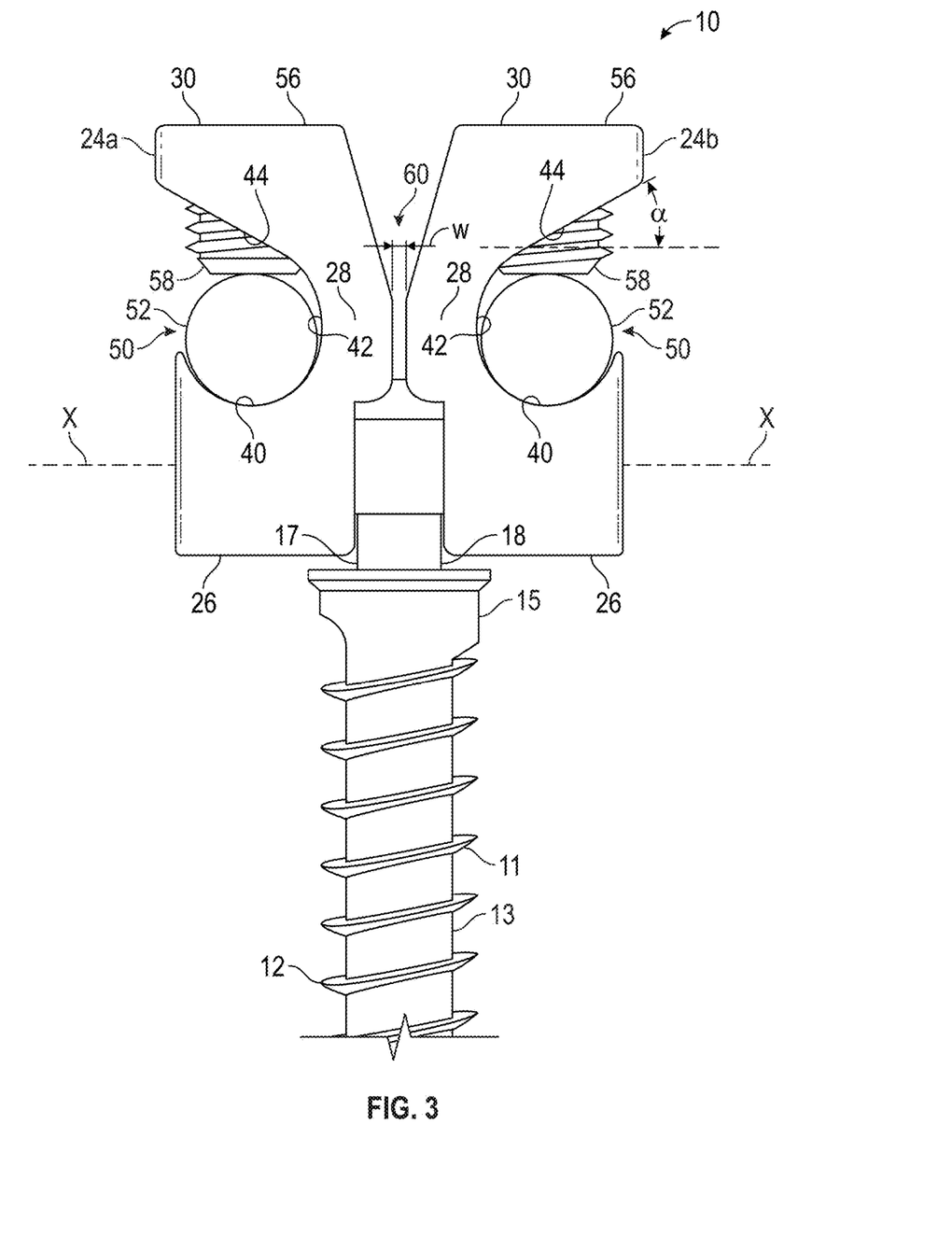
FIG. 3 is an enlarged front view of a portion of the double-headed pedicle screw illustrated in FIG. 1.

Referring now to the drawings, there is illustrated in FIGS. 1-3 a first embodiment of a pedicle screw, indicated generally at 10, in accordance with this invention. The illustrated pedicle screw 10 may, for example, be used in connection with a posterior dynamic stabilization system or any other alignment or immobilization structure.

Referring again to FIGS. 1-3, the pedicle screw 10 includes a shaft portion 11 having a shaft helical thread 12 provided on an outer surface 13 thereof. In the illustrated embodiment, the shaft helical thread 12 extends from a lower tapered tip 14 of the shaft portion 11 toward an upper end 15 thereof, although such is not required. The shaft helical thread 12 is configured to be secured to a vertebra of a spine (not shown). The shaft helical thread 12 can have any desired thread pitch, thread depth, root diameter and thread diameter sufficient to secure the shaft portion 11 to a vertebra of a spine.

Referring again to FIGS. 1-3, the upper end 15 of the shaft portion 11 of the pedicle screw 10 includes a plurality of protrusions 16 provided thereon. In the illustrated embodiment, two of such protrusions 16 extend outwardly from first and second opposed sides 17 and 18, respectively, of the upper end 15 of the shaft portion 11 of the pedicle screw 10, although such is not required.

Referring again to FIGS. 1-3, the pedicle screw 10 includes a plurality of yoke assemblies 24a, 24b attached to the upper end 15 of the shaft portion 11. The yoke assemblies 24a, 24b include a lower segment 26, an intermediate segment 28 extending from the lower segment 26 and an upper segment 30 extending from the intermediate segment 28. As will be explained in more detail below, each of the yoke assemblies 24a, 24b is configured for pivoting movement relative to a sagittal plane, independent of any pivoting movement of an adjacent yoke assembly. In the embodiment illustrated in FIGS. 1-3, the yoke assemblies 24a, 24b are formed as a one-piece, unitary body. However, it is contemplated that in other embodiments, the lower segment 26, intermediate segment 28 and upper segment 30 of the yoke assemblies 24a, 24b can be formed as discrete elements that are subsequently assembled together.

Referring now to FIGS. 1 and 2, the lower segment 26 of the yoke assemblies 24a, 24b includes apertures 32, extending from an inner surface 34 of the lower segments 26 to an outer surface 36. The apertures 32 are sized and shaped such as to receive the protrusions 16. In the illustrated embodiment, the apertures 32 have a circular cross-sectional shape corresponding to a circular cross-sectional shape of the protrusions 16. However, in other embodiments, the apertures 32 can be other cross-sectional shapes sufficient to receive the cross-sectional shape of the plurality of protrusions 16. The apertures 32 and the protrusions 16 cooperate, such as to allow pivoting movement of the yoke assemblies 24a, 24b about a longitudinal axis X-X of the protrusions 16. The pivoting movement of the yoke assemblies 24a, 24b about the longitudinal axis X-X results in an arcuate movement of the intermediate and upper segments 28, 30 of the yoke assemblies 24a, 24b along a Y-Y axis, thereby allowing adjustment in the connection to a rod or other alignment or immobilization structures. Advantageously, each of the yoke assemblies 24a, 24b is configured to rotate about its respective protrusion independent from the rotation of the other yoke assembly.

Referring again to FIGS. 1-3, the lower segment 26 includes an upper surface 40, the intermediate segment 28 includes an outer surface 42 and the upper segment 30 includes a lower surface 44. The upper surface 40 of the lower segment 26, outer surface 42 of the intermediate segment 28 and the lower surface 44 of the upper segment 30 cooperate to form a recess 50 therebetween. In the embodiment shown in FIGS. 1-3, the recess 50 has the cross-sectional shape of a "C", with the opening of the "C" facing away from the opposing sides 17, 18 of the upper end 15 of the shaft portion 11.

Referring again to FIGS. 1-3, the recesses 50 are configured to receive portions of conventional rods 52 (shown in FIG. 3) or other alignment or immobilization structures therein. In the illustrated embodiment, the upper surface 40 of the lower segment 26 and the outer surface 42 of the intermediate segment 28 have an arcuate cross-sectional shape configured to receive a circular cross-sectional shape of the rod 52. In other embodiments, the upper surface 40 of the lower segment 26 and the outer surface 42 of the intermediate segment 42 can have other cross-sectional shapes configured to receive corresponding cross-sectional shapes of the rod 52.

Referring again to the embodiment illustrated in FIGS. 1-3, the lower surface 44 of the upper segment 30 has a substantially linear cross-sectional shape and extends from the outer surface 42 of the intermediate segment 28 at an angle $\alpha$ in a range of from about 25° to about 60°. The substantially linear cross-sectional shape of the lower surface 44 of the upper segment 30 and the angle $\alpha$ are configured to facilitate entry of the rod 52 into the recess 50. It should be appreciated that in other embodiments, the lower surface 44 of the upper segment 30 can have other cross-sectional shapes and the lower surface 44 of the upper segment 30 can extend from the outer surface 42 of the intermediate segment 28 at other angles, sufficient to facilitate entry of the rod 52 into the recess 50.

Referring again to FIG. 3, it is contemplated that each of the recesses 50 may receive separate portions of a single alignment or immobilization structure therein or each of the recesses 50 may receive portions of separate alignment or immobilization structures therein.

Referring again to FIGS. 1 and 2, the upper segment 30 of each yoke assembly 24a, 24b includes an aperture 54 extending from an upper surface 56 to the lower surface 44 there through. The aperture 54 is configured to receive a fastener 58. The fastener 58 is configured to secure the rod 52 against the upper surface 40 of the lower segment 26. In the illustrated embodiment, the fastener 58 is a set screw. However, in other embodiments, the fastener 58 can be other structures, mechanisms and devices, such as for example pins, clips and clamps, sufficient to secure the rod 52 against the upper surface 40 of the lower segment 26.

Referring now to FIGS. 1 and 3, an air gap or clearance gap 60 is formed between intermediate segments 28 of the adjacent yoke assemblies 24a, 24b. The clearance gap 60 is configured to prevent rotational interference of the adjacent yoke assemblies 24a, 24b, thereby facilitating independent pivoting motion. In the illustrated embodiment, the clearance gap 60 has a minimum width W in a range of from about 0.3 mm to about 0.6 mm. However, in other embodiments, the clearance gap 60 can have a minimum width W less than about 0.3 mm or more than about 0.6 mm, sufficient to prevent rotational interference of the adjacent yoke assemblies 24a, 4b and facilitate independent pivoting motion.

Referring again to FIGS. 1-3, the yoke assemblies 24a, 24b are supported on the upper end 15 of the shaft portion 11 and configured for pivoting movement relative to an axis X. As a non-limiting example, the yoke assemblies 24a, 24b may be supported on the upper end 15 of the shaft portion 11 for about ten degrees of pivoting movement relative to a sagittal plane. The term "sagittal plane", as used herein, is defined to mean an anatomical plane which divides a body into right and left halves. It should be appreciated that in other embodiments, the pivoting movement relative to a sagittal plane may be more than or less than about ten degrees. In other embodiments, if desired, such pivoting movement of the yoke assemblies 24a, 24b may be limited to the flexion/extension motion planes. The term "flexion motion plane", as used herein, is defined to mean any angular motions in which two axes of a joint are brought closer together. The term "extension motion planes", as used herein is defined to mean any angular motions in which two axes of a joint are moved further apart. While the yoke assemblies 24a, 24b are described above as being configured for pivoting movement relative to a sagittal plane, it is further contemplated that the yoke assemblies 24a, 24b can be fixed at a desired angle following assembly with alignment or immobilization structures. Fixation of the yoke assemblies 24a, 24b, following receipt of the alignment or immobilization structures, is configured to prevent further pivoting movement.

Figure 4:
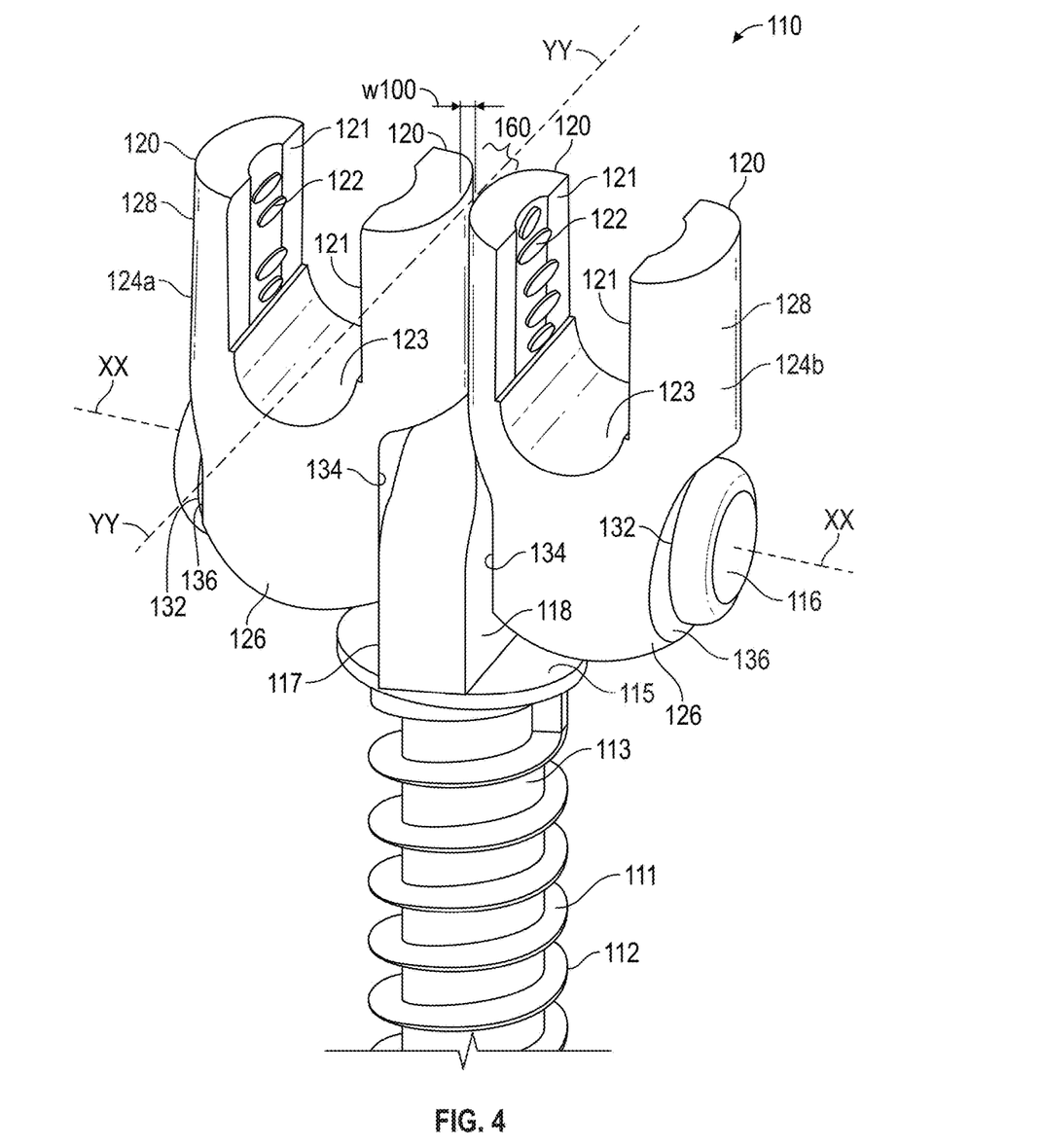
FIG. 4 is an enlarged perspective view of a portion of a second embodiment of a double-headed pedicle screw.
Figure 5:
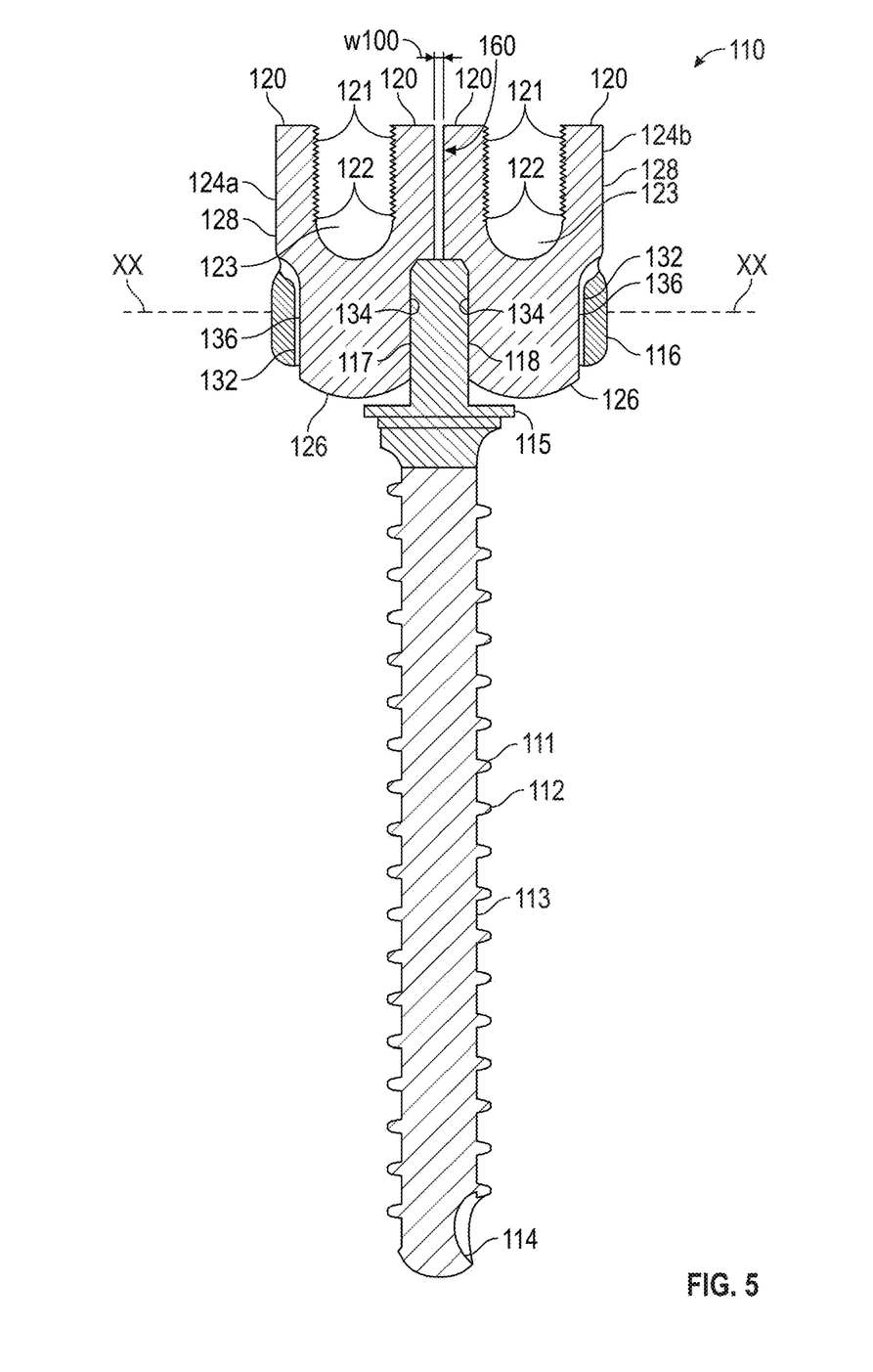
FIG. 5 is a front view of the double-headed pedicle screw illustrated in FIG. 4.

Referring again to FIGS. 1-3, the yoke assemblies 24a, 24b are shown in a first embodiment. However, it should be appreciated that in other embodiments, the yoke assemblies can have other structures, shapes, configurations and orientations. Referring now to FIGS. 4 and 5, a second embodiment of a double-headed pedicle screw (hereafter "pedicle screw") is shown generally at 110.

Referring now to FIGS. 4 and 5, the pedicle screw 110 includes a shaft portion 111 having a shaft helical thread 112 provided on an outer surface 113 thereof. The shaft portion 111 further includes a lower tapered tip 114 and an upper end 115. The upper end 115 of the shaft portion 111 includes a plurality of protrusions 116 provided thereon. In the illustrated embodiment, two of such protrusions 116 extend outwardly from first and second opposed sides 117 and 118, respectively, of the upper end 115 of the shaft portion 111, although such is not required.

In the embodiment illustrated in FIGS. 4 and 5, the shaft portion 111, shaft helical thread 112, outer surface 113, lower tapered tip 114, upper end 115, protrusions 116 and opposed sides 117, 118 are the same as, or similar to, the shaft portion 11, shaft helical thread 12, outer surface 13, lower tapered tip 14, upper end 15, protrusions 16 and opposed sides 17, 18 and shown in FIGS. 1-3 and described above. However, in other embodiments, the shaft portion 111, shaft helical thread 112, outer surface 113, lower tapered tip 114, upper end 115, protrusions 116 and opposed sides 117, 118 can be different from the shaft portion 11, shaft helical thread 12, outer surface 13, lower tapered tip 14, upper end 15, protrusions 16 and opposed sides 17, 18.

Referring again to FIGS. 4 and 5, the pedicle screw 110 further includes a plurality of yoke assemblies 124a, 124b attached to the upper end 115 of the shaft portion 111. Each of the yoke assemblies 124a, 124b includes a lower segment 126 connected to an upper segment 128.

Referring again to FIGS. 4 and 5, the lower segment 126 of the yoke assemblies 124a, 124b includes apertures 132, extending from an inner surface 134 of the lower segments 126 to an outer surface 136. The apertures 132 are sized and shaped such as to receive the protrusions 116. In the illustrated embodiment, the apertures 132 have a circular cross-sectional shape corresponding to a circular cross-sectional shape of the protrusions 116. However, in other embodiments, the apertures 132 can be other cross-sectional shapes sufficient to receive the cross-sectional shape of the protrusions 116. The apertures 132 and the protrusions 116 cooperate, such as to allow pivoting movement of the yoke assemblies 124a, 124b about a longitudinal axis XX-XX of the protrusions 116. The pivoting movement of the yoke assemblies 124a, 124b about the longitudinal axis XX-XX results in an arcuate movement of the upper segments 128 of the yoke assemblies 124a, 124b along a YY-YY axis, thereby allowing adjustment in the connection to a rod or other alignment or immobilization structures. Advantageously, each of the yoke assemblies 124a, 124b is configured to rotate about its respective protrusion independent from the rotation of the other yoke assembly.

Advantageously, each of the yoke assemblies 124a, 124b is configured to rotate about its respective protrusion independent from the rotation of the other yoke assembly.

Referring again to FIGS. 4 and 5, each of the upper segments 128 of the yoke assemblies 124a, 124b includes a plurality of opposing legs 120. The opposing legs 120 have a generally arcuate cross-sectional shape with interior surfaces 121. The interior surfaces 121 of the opposing legs 120 include a helical thread 122, configured to receive a portion of a fastener (not shown).

Referring again to FIGS. 4 and 5, the opposing legs 120 define a recess 123. The recess 123 is configured to receive a portion of a conventional rod (not shown) or other alignment or immobilization structures therein. In the embodiment shown in FIGS. 4 and 5, the recess 123 has the cross-sectional shape of a "U", with the opening of the "U" facing in a substantially vertical direction away from the shaft portion 111. With a portion of the conventional rod or other alignment or immobilization structures positioned in the recess 123, a fastener in cooperation with the helical threads 122 can be configured to secure the rod or other alignment or immobilization structures in the recess 123. In the illustrated embodiment, the fastener is a set screw. In alternate embodiments, the fastener can be other structures, mechanisms or devices, including the non-limiting examples of clips and clamps.

Referring again to FIGS. 4 and 5, it is contemplated that each of the recesses 123 may receive separate portions of a single alignment or immobilization structure therein or each of the recesses 123 may receive portions of separate alignment or immobilization structures therein.

Referring again to FIGS. 4 and 5, an air gap or clearance gap 160 is formed between upper segments 128 of the adjacent yoke assemblies 124a, 124b. The clearance gap 160 is configured to prevent rotational interference of the adjacent yoke assemblies 124a, 124b, thereby facilitating independent pivoting motion. In the illustrated embodiment, the clearance gap 160 has a minimum width W100 in a range of from about 0.3 mm to about 0.6 mm. However, in other embodiments, the clearance gap 160 can have a minimum width W100 less than about 0.3 mm or more than about 0.6 mm, sufficient to prevent rotational interference of the adjacent yoke assemblies 124a, 124b and facilitate independent pivoting motion.

Referring again to FIGS. 4 and 5, the yoke assemblies 124a, 124b are supported on the upper end 115 of the shaft portion 111 and configured for pivoting movement relative to the axis XX-XX. As a non-limiting example, the yoke assemblies 124a, 124b may be supported on the upper end 115 of the shaft portion 111 for about ten degrees of pivoting movement relative to a sagittal plane. It should be appreciated that in other embodiments, the pivoting movement relative to a sagittal plane may be more than or less than about ten degrees. In other embodiments, if desired, such pivoting movement of the yoke assemblies 124a, 124b may be limited to the flexion/extension motion planes.

Figure 6:
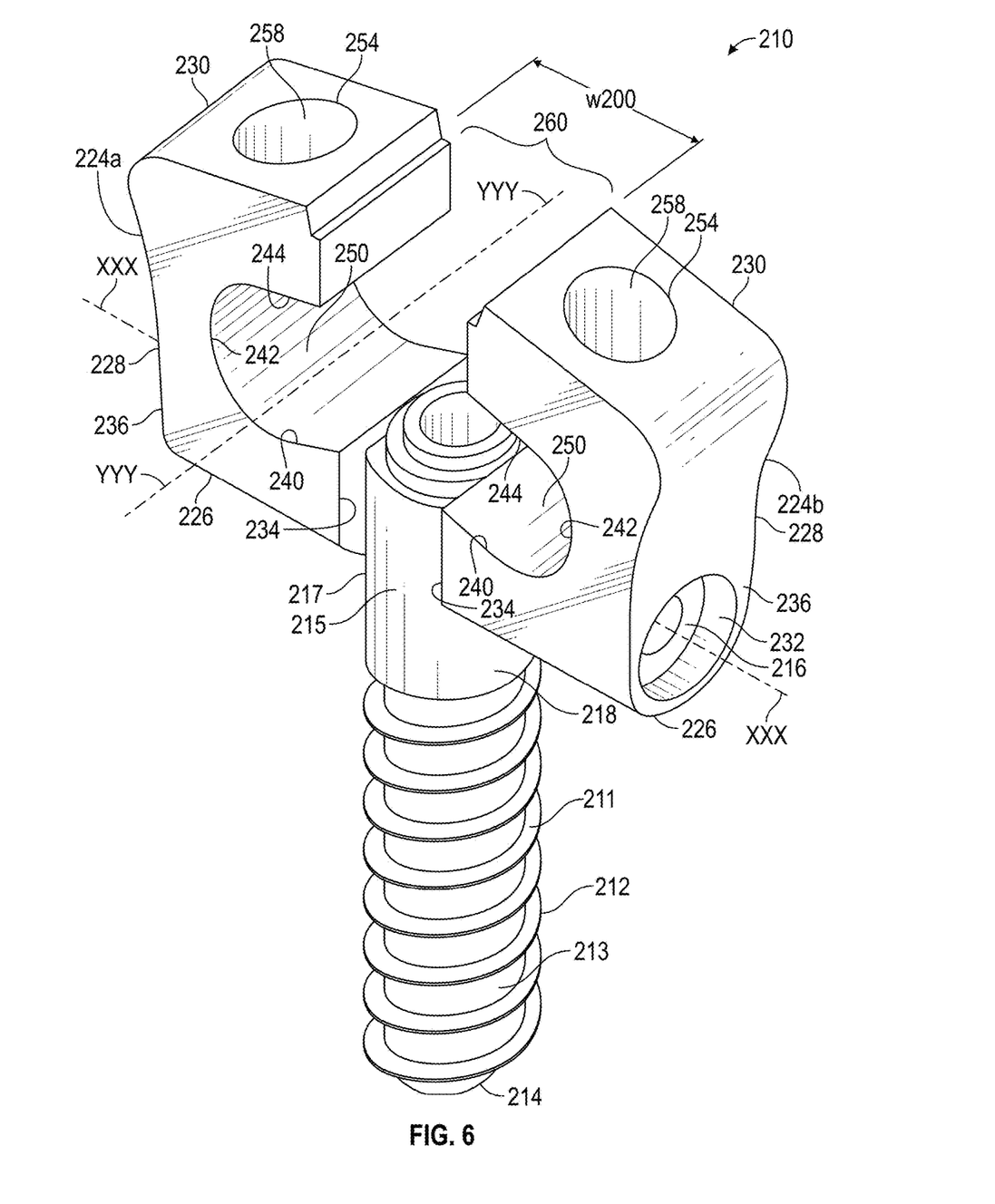
FIG. 6 is a perspective view of a third embodiment of a double-headed pedicle screw in accordance with this invention.
Figure 7:
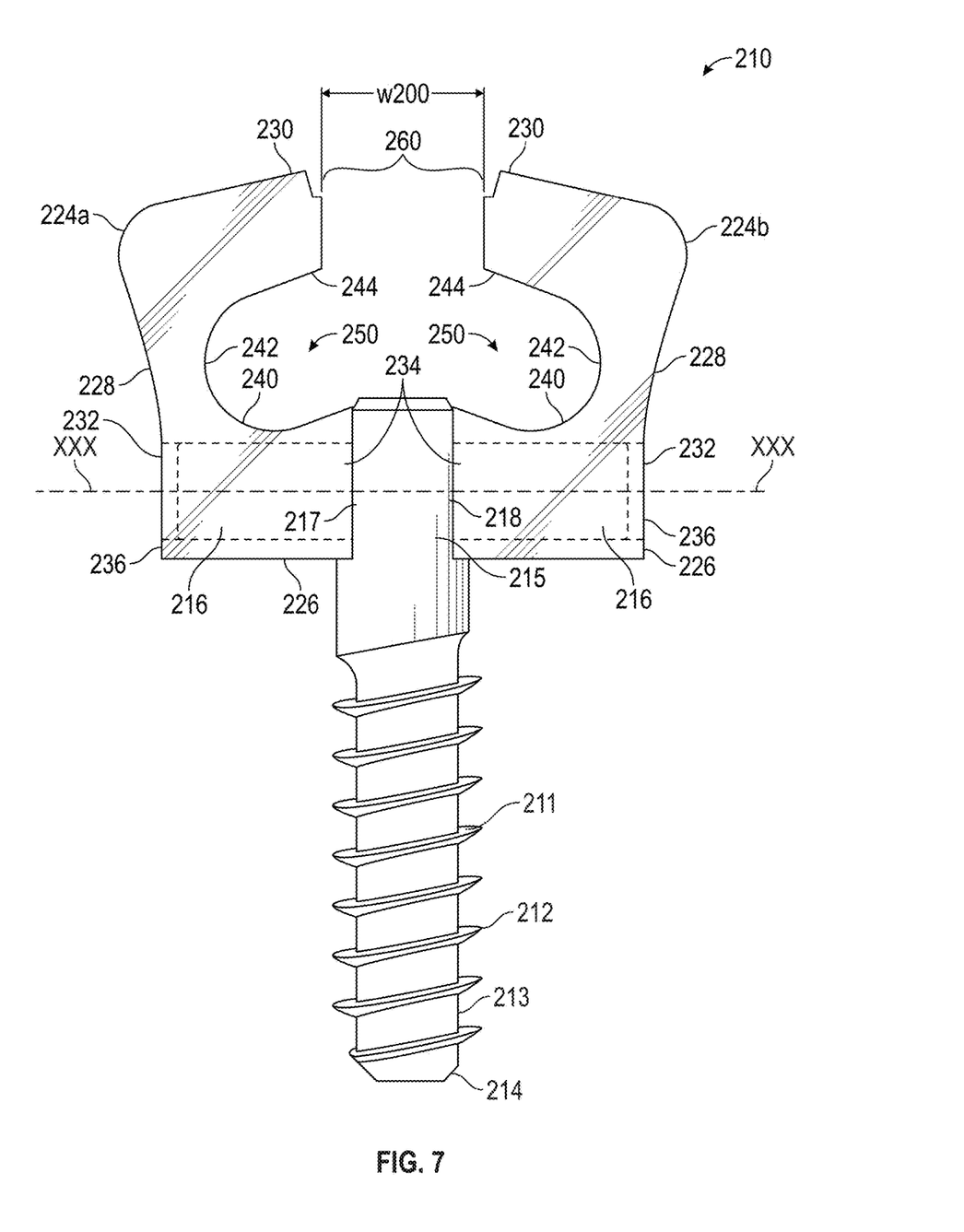
FIG. 7 is an enlarged front view of the double-headed pedicle screw illustrated in FIG. 6.

Referring now to FIGS. 6 and 7, a third embodiment of a double-headed pedicle screw (hereafter "pedicle screw") is shown generally at 210. The pedicle screw 210 includes a shaft portion 211 having a shaft helical thread 212 provided on an outer surface 213 thereof. The shaft portion 111 further includes a lower tapered tip 214 and an upper end 215. The upper end 215 of the shaft portion 211 includes a plurality of protrusions 216 provided thereon. In the illustrated embodiment, two of such protrusions 216 extend outwardly from first and second opposed sides 217 and 218, respectively, of the upper end 215 of the shaft portion 211, although such is not required.

In the embodiment illustrated in FIGS. 6 and 7, the shaft portion 211, shaft helical thread 212, outer surface 213, lower tapered tip 214, upper end 215, protrusions 216 and opposed sides 217, 218 are the same as, or similar to, the shaft portion 11, shaft helical thread 12, outer surface 13, lower tapered tip 14, upper end 15, protrusions 16 and opposed sides 17, 18 and shown in FIGS. 1-3 and described above. However, in other embodiments, the shaft portion 211, shaft helical thread 212, outer surface 213, lower tapered tip 214, upper end 215, protrusions 216 and opposed sides 217, 218 can be different from the shaft portion 11, shaft helical thread 12, outer surface 13, lower tapered tip 14, upper end 15, protrusions 16 and opposed sides 17, 18.

Referring again to FIGS. 6 and 7, the pedicle screw 210 further includes a plurality of yoke assemblies 224a, 224b attached to the upper end 215 of the shaft portion 211. The yoke assemblies 224a, 224b include a lower segment 226, an intermediate segment 228 extending from the lower segment 226 and an upper segment 230 extending from the intermediate segment 228.

Referring again to FIGS. 6 and 7, the lower segment 226 of the yoke assemblies 224a, 224b includes apertures 232, extending from an inner surface 234 of the lower segments 226 to an outer surface 236. The apertures 32 are sized and shaped such as to receive the protrusions 216. In the illustrated embodiment, the apertures 232 have a circular cross-sectional shape corresponding to a circular cross-sectional shape of the protrusions 216. However, in other embodiments, the apertures 232 can be other cross-sectional shapes sufficient to receive the cross-sectional shape of the plurality of protrusions 216. The apertures 232 and the protrusions 216 cooperate, such as to allow pivoting movement of the yoke assemblies 224a, 224b about a longitudinal axis XXX-XXX of the protrusions 216. The pivoting movement of the yoke assemblies 224a, 224b about the longitudinal axis XXX-XXX results in an arcuate movement of the intermediate and upper segments 228, 230 of the yoke assemblies 224a, 224b along a YYY-YYY axis, thereby allowing adjustment in the connection to a rod or other alignment or immobilization structures. Advantageously, each of the yoke assemblies 224a, 224b is configured to rotate about its respective protrusion independent from the rotation of the other yoke assembly.

Referring again to FIGS. 6 and 7, the lower segment 226 includes an upper surface 240, the intermediate segment 228 includes an inner surface 242 and the upper segment 230 includes a lower surface 244. The upper surface 240 of the lower segment 226, outer surface 242 of the intermediate segment 228 and the lower surface 244 of the upper segment 230 cooperate to form a recess 250 therebetween. In the embodiment shown in FIGS. 6 and 7, the recess 250 has the cross-sectional shape of a "C", with the opening of the "C" facing toward the opposing yoke assembly. It should be apparent that the yoke assemblies 224a, 224b are substantially the same, or similar to, the yoke assemblies 24a, 24b illustrated in FIGS. 1-3 and described above with the difference that the opening of the "C" shaped recess 250 is turned 180° from the opening of the "C" shaped recess 50.

In the embodiment shown in FIGS. 6 and 7, the recesses 250 are the same as, or similar to the recesses 50 shown in FIGS. 1-3 and described above. However, it is contemplated that in other embodiments, the recesses 250 can be different from the recesses 50.

In the embodiment shown in FIGS. 6 and 7, the upper surface 240 of the lower segment 226, the inner surface 242 of the intermediate segment 228 and the lower surface 244 of the upper segment 230 are the same as, or similar to, the upper surface 40 of the lower segment 26, the inner surface 42 of the intermediate segment 28 and the lower surface 44 of the upper segment 30. In alternate embodiments, the upper surface 240 of the lower segment 226, the inner surface 242 of the intermediate segment 228 and the lower surface 244 of the upper segment 230 can be different from the upper surface 40 of the lower segment 26, the inner surface 42 of the intermediate segment 28 and the lower surface 44 of the upper segment 30.

Referring again to FIGS. 6 and 7, it is contemplated that each of the recesses 250 may receive separate portions of a single alignment or immobilization structure therein or each of the recesses 250 may receive portions of separate alignment or immobilization structures therein.

Referring again to FIGS. 6 and 7, the upper segment 230 of each yoke assembly 224a, 224b includes an aperture 254 extending there through. The aperture 254 is configured to receive a fastener 258. In the illustrated embodiment, the aperture 254 and the fastener 258 are the same as, or similar to, the aperture 54 and the fastener 58 illustrated in FIGS. 1-3 and described above. However, in other embodiments, the aperture 254 and the fastener 258 can be different from the aperture 54 and the fastener 58.

Referring now to FIGS. 6 and 7, an air gap or clearance gap 260 is formed between upper segments 230. The clearance gap 260 extends such as to be fluidly connected to the recesses 250 in each of the yoke assemblies 224a, 224b. The clearance gap 260 is configured as a conduit to the recesses 250 such that conventional rods or other alignment or immobilization structures can pass between the yoke assemblies 224a, 224b and be seated in the recesses 250. In the illustrated embodiment, the clearance gap 260 has a minimum width W200 in a range of from about 1.0 mm to about 6.0 mm. However, in other embodiments, the clearance gap 260 can have a minimum width W200 less than about 1.0 mm or more than about 6.0 mm, sufficient to be a conduit to the recesses 250 such that conventional rods or other alignment or immobilization structures can pass between the yoke assemblies 224a, 224b and be seated in the recesses 250.

Referring again to FIGS. 6 and 7, the yoke assemblies 224a, 224b are supported on the upper end 215 of the shaft portion 211 and configured for pivoting movement relative to an axis XXX-XXX. As a non-limiting example, the yoke assemblies 224a, 224b may be supported on the upper end 215 of the shaft portion 211 for about ten degrees of pivoting movement relative to a sagittal plane. It should be appreciated that in other embodiments, the pivoting movement relative to a sagittal plane may be more than or less than about ten degrees. In other embodiments, if desired, such pivoting movement of the yoke assemblies 224a, 224b may be limited to the flexion/extension motion planes.

While the embodiments of the double-headed pedicle screw shown in FIGS. 1-7 illustrate the screws 10, 100 and 200 as having yoke assemblies of a generally consistent structure and design, it is within the contemplation of the invention that a pedicle screw can have adjacent yoke assemblies with different structures and configured for different purposes.

The principle and mode of operation of the double-headed pedicle screw have been explained and illustrated in its preferred embodiments. However, it must be understood that the double-headed pedicle screw may be practiced otherwise than as specifically explained and illustrated without departing from its spirit or scope.

What is claimed is:

1. A double-headed pedicle screw comprising:
   a threaded shaft portion having an upper end, the upper end having a first side and an opposing second side, the first side having a first side protrusion and the opposing second side having a second side protrusion; and
   a first yoke assembly extending from the first side of the upper end of the threaded shaft portion;
   a second yoke assembly extending from the opposing second side of the upper end of the threaded shaft portion, each of the first and second yoke assemblies including a recess configured to receive a portion of a rod therein, the recess of the first yoke assembly and the recess of the second yoke assembly each having an opening facing in a direction away from the other yoke assembly;
   wherein the first side protrusion is configured to receive the first yoke assembly and the second side protrusion is configured to receive the second yoke assembly, the first side protrusion and the second side protrusion aligned along a common axis, each of the first and second yoke assemblies configured for pivoting movement relative to the threaded shaft portion independent of the pivoting movement of the other yoke assembly and wherein the first and second yoke assemblies are configured for pivoting movement in a direction perpendicular to the common axis of the first and second side protrusions.

2. The double-headed pedicle screw of claim 1, wherein the protrusions each have a portion with a circular cross-sectional shape.

3. The double-headed pedicle screw of claim 1, wherein the pivoting movement of the yoke assemblies has a maximum of about ten degrees relative to a sagittal plane.

4. The double-headed pedicle screw of claim 1, wherein a fastener is configured to secure the portion of a rod within each of the recesses.

5. The double-headed pedicle screw of claim 4, wherein the fastener is a set screw.

6. The double-headed pedicle screw of claim 1, wherein a gap is formed between adjacent yoke assemblies and configured to prevent rotational interference of the adjacent yoke assemblies.

7. The double-headed pedicle screw of claim 6, wherein the gap has a minimum width in a range of from about 0.3 mm to about 0.6 mm.

8. The double-headed pedicle screw of claim 1, wherein the recesses of the yoke assemblies have the cross-sectional shape of a "C".

9. The double-headed pedicle screw of claim 1, wherein each of the yoke assemblies has a lower segment configured to seat on one of the protrusions.

10. The double-headed pedicle screw of claim 9, wherein each of the yoke assemblies includes an intermediate segment extending from the lower segment and an upper segment extending from the intermediate segment.

11. The double-headed pedicle screw of claim 10, wherein the lower segment, intermediate segment and upper segment of each of the yoke assemblies cooperate to form the recess.

* * * * *